(12) United States Patent
Eng et al.

(10) Patent No.: US 9,149,188 B2
(45) Date of Patent: Oct. 6, 2015

(54) SYSTEMS AND METHODS FOR SYNCHRONIZING DATA RECEIVED FROM MULTIPLE SENSOR MODULES IN A PATIENT MONITOR SYSTEM

(75) Inventors: William Eng, Union, NJ (US); Daniel A. Zahner, Pompton Plains, NJ (US); Frank Menzel, Oakland, NJ (US)

(73) Assignee: SHENZHEN MINDRAY BIO-MEDICAL ELECTRONICS CO. LTD., Shenzhen (CN)

( * ) Notice: Subject to any disclaimer, the term of this patent is extended or adjusted under 35 U.S.C. 154(b) by 744 days.

(21) Appl. No.: 12/829,216

(22) Filed: Jul. 1, 2010

(65) Prior Publication Data

US 2012/0004516 A1 Jan. 5, 2012

(51) Int. Cl.
*G06F 19/00* (2011.01)
*A61B 5/00* (2006.01)

(52) U.S. Cl.
CPC ............. *A61B 5/0015* (2013.01); *A61B 5/0024* (2013.01); *A61B 5/7221* (2013.01); *A61B 5/742* (2013.01); *G06F 19/3412* (2013.01)

(58) Field of Classification Search
None
See application file for complete search history.

(56) References Cited

U.S. PATENT DOCUMENTS

| | | | | |
|---|---|---|---|---|
| 4,560,985 A * | 12/1985 | Strecker et al. | ................ | 370/447 |
| 5,027,297 A * | 6/1991 | Garitty et al. | ................ | 702/187 |
| 5,807,245 A * | 9/1998 | Aldestam et al. | ............. | 600/300 |
| 7,133,800 B2 * | 11/2006 | Delin et al. | .................... | 702/125 |
| 2006/0089541 A1 * | 4/2006 | Braun et al. | .................. | 600/300 |
| 2007/0285531 A1 * | 12/2007 | Watanabe et al. | ........... | 348/223.1 |
| 2008/0133168 A1 * | 6/2008 | Barrett | .......................... | 702/121 |
| 2009/0105552 A1 * | 4/2009 | Nishiyama et al. | ........... | 600/300 |
| 2011/0152632 A1 * | 6/2011 | Le Neel et al. | ................ | 600/300 |

* cited by examiner

*Primary Examiner* — William Thomson
*Assistant Examiner* — Davin Sands
(74) *Attorney, Agent, or Firm* — Kory D. Christensen; Stoel Rives LLP

(57) ABSTRACT

A patient monitor system synchronizes patient data acquired by a plurality of sensor modules. Patient data from the sensor modules are synchronized by transmitting, from a patient monitor host, a start message that each newly connected sensor module uses to determine when to begin transmitting patient data to the patient monitor host. At a predetermined count interval, the patient monitor host also broadcasts an incrementing sequence count value to each of the connected sensor modules. The sensor modules use the sequence count values and the start message to determine when the patient monitor host expects each sensor module to transmit data packets. Each data packet sent by the sensor modules includes a sequence count value that the patient monitor host uses to align the various waveforms for display.

30 Claims, 6 Drawing Sheets

SYSTEMS AND METHODS FOR SYNCHRONIZING DATA RECEIVED FROM MULTIPLE SENSOR MODULES IN A PATIENT MONITOR SYSTEM

TECHNICAL FIELD

The present disclosure relates to patient monitor systems.

DETAILED DESCRIPTION

Figure 1:
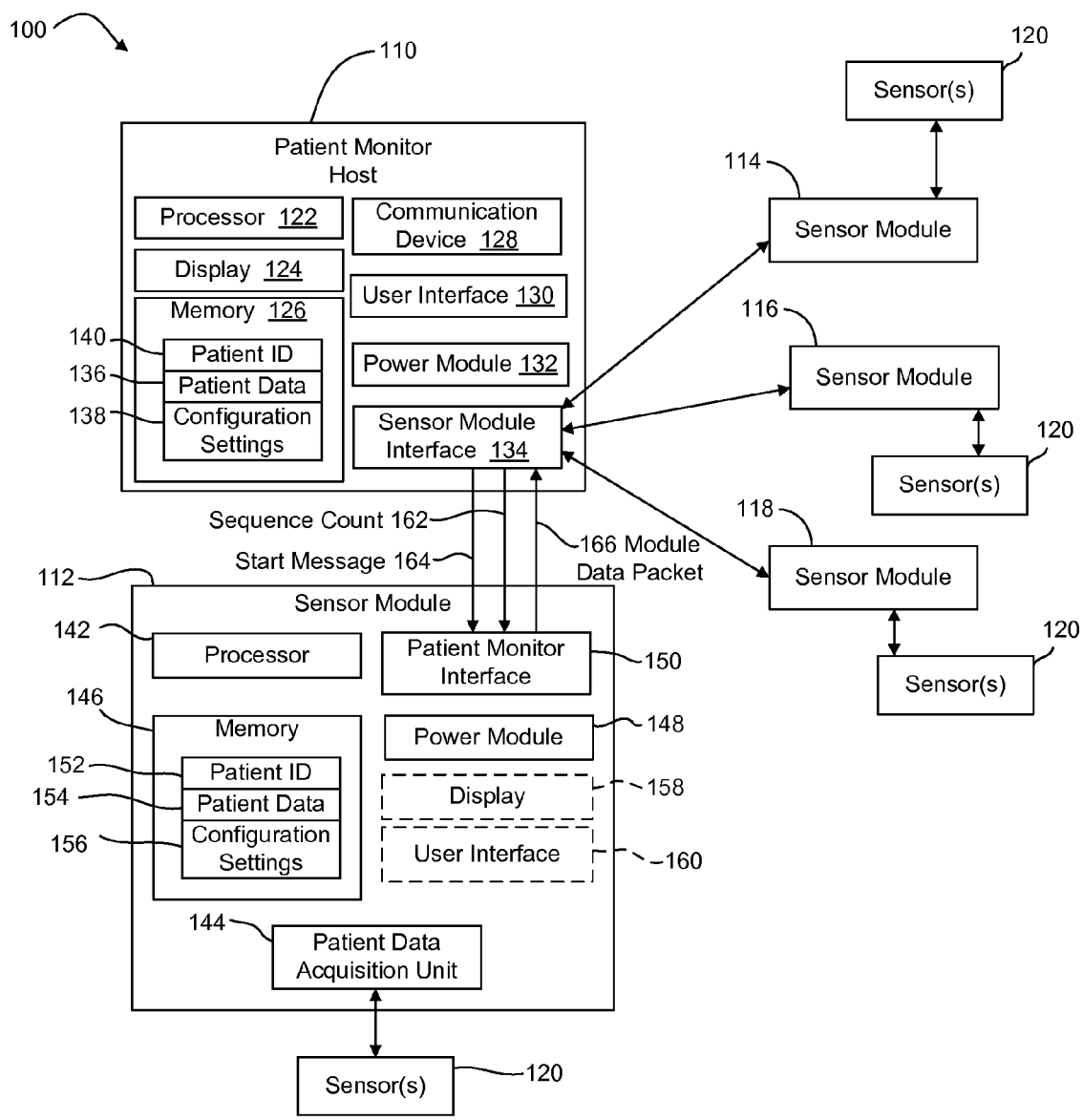
FIG. 1 is a block diagram of a patient monitoring system according to one embodiment.

Patient monitors are used to receive, analyze, and display data from sensors attached to a patient. The patient data may include, for example, pulse, temperature, respiration, blood pressure (e.g., non-invasive blood pressure (NIBP)), blood oxygen (e.g., saturation of peripheral oxygen ($SpO_2$)), electrocardiogram (ECG), and other types of patient data. In certain embodiments disclosed herein, sensor modules receive patient data from leads connected to sensors attached to the patient and are configured to be selectively coupled to a main patient monitor or host. Each sensor module may be configured for a different type of patient data. At least some of the sensor modules may be portable to allow continuous monitoring when transporting a patient, including while transporting a patient between hospital wards or rooms with respective patient monitor hosts. For a particular patient, a patient monitor host processes patient data signals received from the sensor modules and displays the patient data signals (e.g., as waveforms and/or numeric parameter data) on a display device.

For medical diagnosis and monitoring, it is useful for the displayed patient data to be synchronized across some or all of the waveforms that have been collected on a particular patient. Many types of communication systems and protocols, however, do not provide sufficient time synchronization of data collected and communicated from different nodes in a network. Even systems that use a global system clock, for example, are subject to clock drift between nodes and may be difficult to use with patient monitor systems where different sensor modules are frequently connected and disconnected from the system. Other types of communication systems do not attempt to guarantee delivery times of messages sent between network nodes. In other words, a message sent from one node may arrive at two receiving nodes at different times.

Thus, in certain embodiments disclosed herein, patient data from a plurality of sensor modules are synchronized by transmitting, from a patient monitor host, a start message that each newly connected sensor module uses to determine when to begin transmitting patient data to the patient monitor host. The start message may be a function call that allows the patient monitor host to inform the sensor modules whether to enter a monitoring mode or a diagnostics mode, and includes a current time and a start value used to synchronize the sending of collected data. At a predetermined count interval, the patient monitor host also broadcasts an incrementing sequence count value to each of the connected sensor modules. As used herein, the term "increment" or "incrementing" refers to a periodic change in values that includes increasing values or decreasing values.

The sensor modules use the sequence count values as a time base (e.g., in milliseconds) and the start value as a reference time to determine when the patient monitor host expects each sensor module to transmit data packets. When a new sensor module connects to the system, it uses an updated start value transmitted by the patient monitor host to determine when to transmit data packets at regular intervals that are matched in time with the other sensor modules in the system. Each data packet sent by the sensor modules includes a sequence count value that the patient monitor host uses to align the various waveforms for display.

In an example embodiment described herein, synchronized communication is provided using a universal serial bus (USB). An artisan will recognize, however, that the disclosure is not limited to USB embodiments and that any communication system or protocol may be used that provides, or that is adapted to provide, an incrementing count, such as a frame count, to network nodes.

In the example USB embodiment, a USB controller in the patient monitor host provides an 11-bit USB sequence count to each of the sensor modules regardless of any particular sensor module's time of insertion into the system. The USB sequence count is used to synchronize the data collection of the sensor modules in the system. On registration of a first USB enabled sensor module, the USB controller in the patient monitor host sends the USB sequence count (X) to the first sensor module as its starting point. The first sensor module then begins sending data when the running USB count (which increments, e.g., every 1 millisecond) is equal to (X). The first data from the first sensor module includes waveform data and numeric parameter data. From then on, the first sensor module uses the millisecond USB sequence count to send waveform data at a predetermined waveform data interval (e.g., 50 milliseconds) and the numeric parameter data at a predetermined parameter data interval (e.g., 1 second).

When a new or additional USB enabled sensor module establishes communications with the USB controller in the patient monitor host, the USB controller registers it with the USB sequence count of the next 1-second interval. Thus, at the next 1-second boundary, the new sensor module sends 50 milliseconds of waveform data and initial numeric parameter data.

In the example embodiment, the USB sequence count (X) is modulus 2048 because it is based on an 11-bit counter that wraps around (e.g., counter values repeat from 0 to 2047). Thus, the sensor modules in the example embodiment do not always start transmitting data when the lower 11 bits=0 or some other fixed value. If the sensor modules were to start transmitting data at a fixed sequence count number (e.g., at 0 or 1000), then the sensor modules would not all register on a global 1-second boundary. Due to the wrapping of the 11-bit counter, the global 1-second boundary may be any number (X). The 1-second boundaries starting from 0 in this example are: 0, 1000, 2000, 952, 1952, 904, 1904, 856, 1856, 808, 1808, . . . . By having the running 1-second start counter sent to each sensor module on initialization, each sensor module starts transmitting its respective waveform data and numeric parameter data on the same global 1-second boundary.

The sensor modules send the USB sequence count to the patient monitor host along with the collected data. The 11-bit USB sequence count may be sent, for example, in a data sequence count field of an MDD header block. The patient monitor host may indentify 1-second boundary USB sequence counts by the fact that the MDD message includes numeric parameter data. By continually monitoring and updating the next 1-second boundary based on the USB sequence count from the attached sensor modules, the proper 1-second count is available for any newly attached sensor modules to register. The patient monitor host uses the USB sequence count to align waveform data from different sensor modules for display to a user.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform the processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/computer-readable medium suitable for storing electronic instructions.

FIG. 1 is a block diagram of a patient monitoring system 100 according to one embodiment. The patient monitoring system 100 includes a patient monitor host 110 in communication with a plurality of sensor modules 112, 114, 116, 118. While FIG. 1 shows four sensor modules, an artisan will recognize from the disclosure herein that system 100 may include any number of sensor modules, including a single sensor module or substantially more than four sensor modules. Each sensor module 112, 114, 116, 118 is connected to one or more sensors 120 (e.g., through one or more leads) configured to acquire respective patient data from the patient (not shown). At least one of the sensor modules 112, 114, 116, 118 may be mobile to allow the patient to be continuously monitored during transportation between different hospital wards or other monitoring locations without being disconnected from one or more sensors 120 and associated leads. Accordingly, the sensor modules 112, 114, 116, 118 are each configured to be selectively coupled with and selectively decoupled from the patient monitor host 110 or a module rack (not shown) that is in communication with the patient monitor host 110.

The patient monitor host 110, according to the example embodiment illustrated in FIG. 1, includes a processor 122, a display device 124, a memory device 126, a communication device 128, a user interface 130, a power module 132, and a sensor module interface 134. The processor 122 is configured to process patient data received through the sensor module interface 134, synchronize the patient data, and display the synchronized patient data (e.g., as waveforms and/or numeric parameter data) in the user interface 130 on the display device 124. An example user interface 130 is discussed below with respect to FIG. 2. The display device 124 may include a liquid crystal display (LCD) or other display screen (not shown).

The sensor module interface 134 receives the patient data through the sensor modules 112, 114, 116, 118, which each communicate with respective sensors 120 attached to the patient. The sensor module interface 134 may be configured to synchronize and process the acquired patient data in cooperation with the processor 122. In an example embodiment, the sensor module interface 134 includes a USB controller. An artisan will recognize from the disclosure herein that the processor 122 and/or the sensor module interface 134, either combined or separately, may include a special purpose processor configured to perform the processes described herein. In another embodiment, the processor 122 and/or sensor module interface 134, either combined or separately, may include a general purpose processor configured to execute computer executable instructions (e.g., stored in a non-transitory computer-readable medium such as the memory device 126) to perform the processes described herein.

The patient monitor host 110 may store the data received from the sensor modules 112, 114, 116, 118 as patient data 136 in the memory device 126 along with other data such as a set of configuration settings 138. The memory device 126 may also include a patient identifier (ID) 140, which may include an index of patient IDs, used to correlate portions of the patient data 136 and/or the configuration settings 138 with particular patients. Thus, different portions of the patient data 136 and/or the configuration settings 138 may correspond to different patient IDs 140.

The communication device 128 is configured to communicate, for example, through a network (not shown) with a central monitoring station (not shown) and/or an external database or memory for storing patient data. In certain embodiments, the communication device 128 is configured to wirelessly communicate with the network.

The power module 132 provides any necessary power conversions and distributes power throughout the patient monitor host 110. The power module 132 may include a battery for mobile use of the patient monitor host 110.

FIG. 1 also shows example components of the sensor module 112. For illustrative purposes, such details are not shown for the sensor modules 114, 116, 118. However, an artisan will understand from the disclosure herein that any of the sensor modules 114, 116, 118 may include the components shown and discussed in relation to the sensor module 112.

The sensor module 112 includes a processor 142, a patient data acquisition unit 144, a memory device 146, a power module 148, and a patient monitor interface 150. The processor 142 is configured to execute computer executable instructions (e.g., stored in a non-transitory computer-readable medium such as the memory device 146) to perform the processes described herein. The memory device 146 may store a patient ID 152 for associating acquired data with particular patients. The patient data acquisition unit 144 is configured to receive patient data signals from the sensors 120.

The patient data acquisition unit 144 may be configured to receive and store different types of patient data signals. For example, the patient data acquisition unit 144 may include different cards, modules, or circuitry for sensing ECG, $SpO_2$, NIBP, and/or temperature data. The patient data acquisition unit 144 stores the patient data signals as patient data 154 in the memory device 146 for subsequent transfer to the patient monitor host 110. In certain embodiments, the sensor module 112 also communicates stored configuration settings 156 to the patient monitor host 110.

The power module 148 may include a battery (not shown) that allows the sensor module 112 to be used in a mobile mode when transporting a patient. The power module 148 may also include circuitry (not shown) for charging the battery and/or operating the sensor module 112 with power received from the power module 132 of the patient monitor host 110.

In one embodiment, the sensor module 112 includes an optional display device 158 and a user interface 160 that allow the sensor module 112 to operate in a monitor mode. When decoupled from the patient monitor host 110, for example, the sensor module 112 may function with limited monitor capabilities. The display device 158 may include a small LCD or other display screen (not shown). The user interface 160 allows the user to view at least some of the configuration settings, alarm settings, and patient data values. The display device 158 and the user interface 160 may also provide information such as a patient ID, sensor module ID, sensor ID(s), user ID, and last coupled patient monitor ID. The display device 158 and/or the user interface 160 may also allow the user to silence an alarm or enter user data. To maintain the portability of the sensor module 112 and/or to reduce costs, in certain embodiments, the display device 158 and the user interface 160 of the sensor module 112 provide limited functionality for use during transporting patients. For example, in certain embodiments, the user may not be able to configure alarms through the sensor module 112.

The patient monitor interface 150 in the sensor module 112 communicates the collected patient data 154 to the sensor module interface 134 in the patient monitor host 110. In certain embodiments, the patient monitor interface 150 includes a USB device. Although not shown in FIG. 1, the sensor modules 114, 116, 118 also communicate their respective patient data (e.g., waveform data and numeric parameter data) to the sensor module interface 134 in the patient monitor host 110. The sensor module interface 134 cooperates with the sensor modules 112, 114, 116, 118 to synchronize the acquired patient data for display on the display device 124.

For example, the sensor module interface 134 transmits an incrementing sequence count 162 to the patient monitor interface 150 in the sensor module 112 and to each of the other connected sensor modules 114, 116, 118. The sensor modules 112, 114, 116, 118 use the incrementing sequence count 162 as a time base (e.g., in milliseconds) to determine the completion of respective predetermined intervals for transmitting waveform data and numeric parameter data to the sensor module interface 134.

When the patient monitor interface 150 in the sensor module 112 initially connects to the sensor module interface 134 (or reconnects after being disconnected), a registration process identifies the sensor module 112 and the type of data provided by the sensor module 112 (e.g., heart rate, blood pressure, temperature, etc.) to the patient monitor host 110.

As part of the registration process, the sensor module interface 134 sends a start message 164 to the patient monitor interface 150 that the sensor module 112 uses to determine when to start transmitting the patient data 154 to the patient monitor host 110 as a module data packet 166. Once the sensor module 112 begins transmitting the patient data 154 to the patient monitor host 110, the patient monitor interface 150 includes a data count value (e.g., a copy of the current sequence count value 162) along with the patient data 154 in the module data packets 166. The patient monitor host 110 matches the data count values received from the patient monitor interface 150 in the sensor module 112 with data count values received from the other sensor modules 114, 116, 118 to align waveform data in the user interface 130 displayed on the display device 124. For illustrative purposes, the sequence count 162, start message 164, and module data packet 166 are only shown between the sensor module interface 134 and the patient monitor interface 150 but may also be communicated between the sensor module interface 134 and one or more of the other sensor modules 114, 116, 118.

Figure 2:
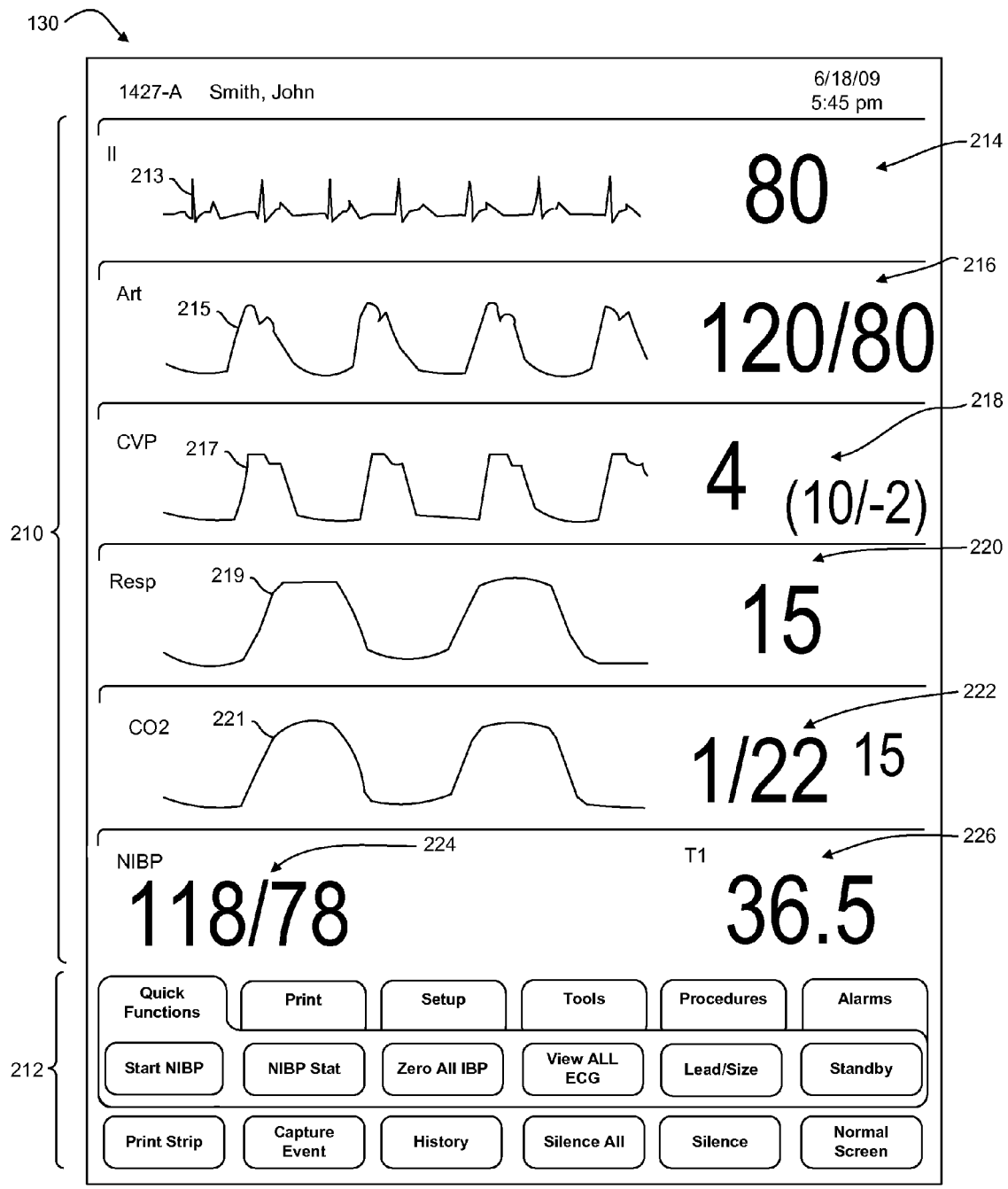
FIG. 2 illustrates an example user interface that may be used according to one embodiment.

FIG. 2 illustrates an example user interface 130 that may be used according to one embodiment. The user interface 130 includes a first area 210 for displaying monitored patient data and a second area 212 for displaying controls and functions used to control and configure a patient monitor system, such as the patient monitor system 100 shown in FIG. 1.

As shown in FIG. 2, the first area 210 may display (e.g., graphically and numerically) information associated with a plurality of different patient parameters. In this example, the displayed patient parameters include a waveform 213 and numeric parameter data 214 corresponding to electrocardiogram (ECG) information (e.g., received through lead II), a waveform 215 and numeric parameter data 216 corresponding to arterial pressure information, a waveform 217 and numeric parameter data 218 corresponding to central venous pressure (CVP) information, a waveform 219 and numeric parameter data 220 corresponding to respiration information, a waveform 221 and numeric parameter data 222 corresponding to carbon dioxide ($CO_2$) level information, numeric parameter data 224 corresponding to non-invasive blood pressure (NIBP) information, and numeric parameter data 226 corresponding to temperature information. An artisan will understand from the disclosure herein that many other types of patient information (both as waveforms and numeric parameter data) may also be displayed.

Because the waveforms 213, 215, 217, 219, 221 generally appear to be continuous, the user interface 130 adds data to the displayed waveforms 213, 215, 217, 219, 221 at relatively high rates as compared to the rate at which the user interface 130 refreshes the display of the numeric parameter data 214, 216, 218, 220, 222, 224, 226. For example, the user interface 130 may add data to the displayed waveforms 213, 215, 217, 219, 221 every 50 milliseconds (the waveform data interval) and update the displayed numeric parameter data 214, 216, 218, 220, 222, 224, 226 only once per second (the parameter data interval). Of course, any other values may be used for the waveform data interval and/or the parameter data interval depending on the particular application.

In some embodiments, at least some of the numeric parameter data is calculated by the patient monitor host 110 from waveform data or other data received from the sensor modules 112, 114, 116, 118. In addition, or in other embodiments, at least some of the numeric parameter data is determined by the respective sensor modules 112, 114, 116, 118 and transmitted to the patient monitor host 110 at the predetermined parameter data interval.

In certain embodiments, the patient monitor host 110 aligns two or more of the waveforms 213, 215, 217, 219, 221 displayed in the user interface 130 based on data count values received from the respective sensor modules 112, 114, 116, 118. Example alignment processes are discussed below with respect to FIGS. 3A, 3B, 4, and 5.

Figure 3A:
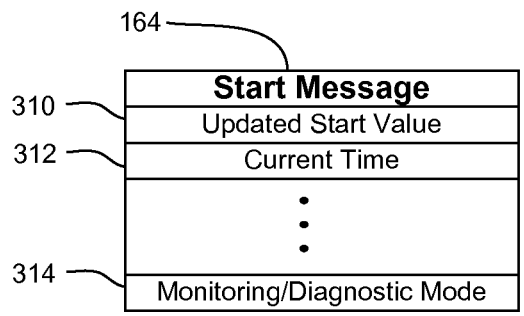
FIG. 3A graphically represents an example data structure of a start message according to one embodiment.

FIG. 3A graphically represents an example data structure of a start message 164 according to one embodiment. The start message 164 includes an updated start value 310 and a current time 312. The start message 164 may include other information used to register a newly connected sensor module. For example, the start message 164 may include a field 314 that indicates whether the newly connected sensor module should enter a monitoring mode or a diagnostics mode.

Figure 3B:
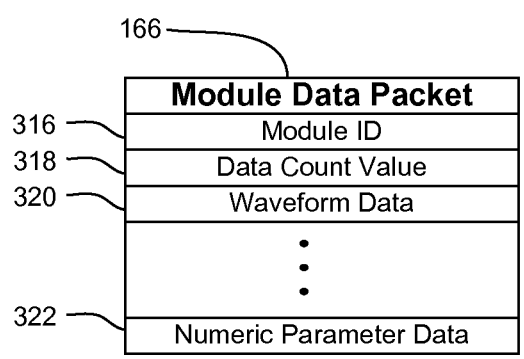
FIG. 3B graphically represents an example data structure of a module data packet according to one embodiment.

FIG. 3B graphically represents an example data structure of a module data packet 166 according to one embodiment. The module data packet 166 includes a module ID 316 that is unique to a particular sensor module, a data count value 318, and waveform data 320. The module data packet 166 may include handshaking or other types of information. Certain module data packets 166 also include numeric parameter data 322. To reduce communication traffic, for example, the sensor modules may only include the numeric parameter data 322 in module data packets 166 that are transmitted at boundaries corresponding to the parameter data interval, which corresponds to the rate at which numeric parameter data is refreshed in the user interface 130 displayed on the display device 124.

Figure 4:
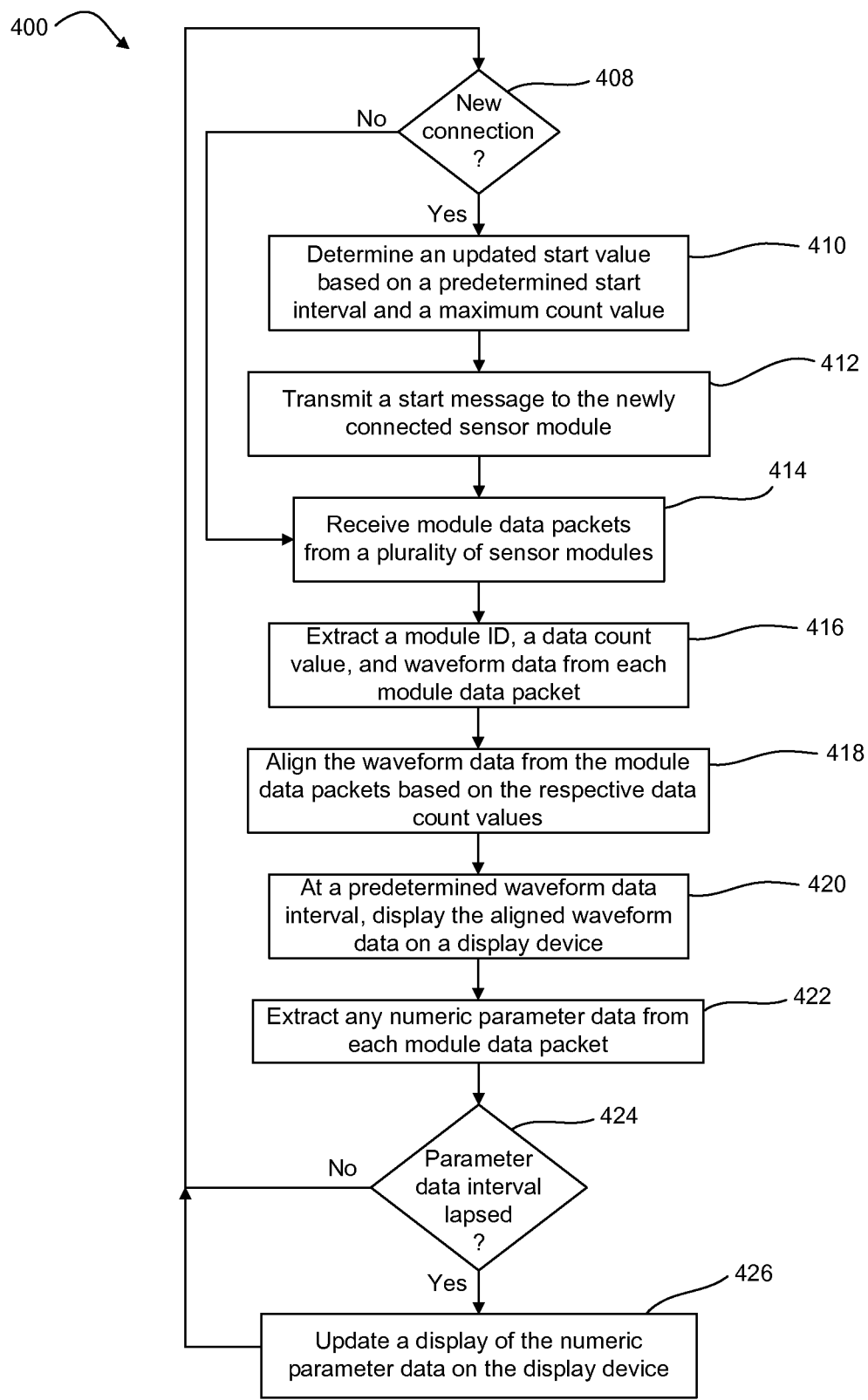
FIG. 4 is a flowchart of a process for synchronizing the display of patient data received from a plurality of sensor modules in a patient monitor system according to one embodiment.

FIG. 4 is a flowchart of a process 400 for synchronizing the display of patient data received from a plurality of sensor modules in a patient monitor system according to one embodiment. The process 400 may be performed, for example, by the patient monitor host 110 shown in FIG. 1. The process 400 includes determining 408 whether there is a new connection between the patient monitor host 110 and a sensor module (e.g., the sensor module 112 shown in FIG. 1). If the patient monitor host 110 does not detect a new connection, then the patient monitor host 110 proceeds to receive 414 module data packets from any previously connected sensor modules.

If there is a new connection, the patient monitor host 110 determines 410 an updated start value 310 based on a predetermined start interval and a maximum count value. The maximum count value may be based on the number of bits used for the counter (e.g., an 11-bit counter has a maximum count value of 2048). In certain embodiments, the updated start value 310 is selected to occur at boundaries corresponding to updating numeric parameter data. In other words, the predetermined start interval corresponds to the parameter data interval and the patient monitor host 110 may determine the updated start value by tracking the data count values 318 at which the sensor modules 114, 116, 118 provide the numeric parameter data 322. For example, if the last module data packets 166 that include numeric parameter data 322 have data count values of "1856," and if the predetermined start interval (or predetermined parameter data interval) is "1000" counts (e.g., 1 second for sequence count values that increase every 1 millisecond), then the patient monitor host 110 determines that the updated start value 310 is "808" (e.g., for a maximum count value of 2048 based on an 11-bit counter). In other embodiments, the patient monitor host 110 determines the updated start value 310 by applying the predetermined start interval and the maximum count value to an initial start value (e.g., starting from a "0" count value).

After determining the updated start value 310, the process 400 includes transmitting 412 a start message 164 from the patient monitor host 110 to the newly connected sensor module 112. The start message 164 includes the updated start value 310 and a current time 312.

The patient monitor host 110 then receives 414 module data packets 166 from a plurality of sensor modules (e.g., the sensor modules 112, 114, 116, 118). The patient monitor host 110 then extracts 416 a module ID 316, a data count value 318, and waveform data 320 from each of the received module data packets 166. The patient monitor host 110 aligns 418 the waveform data 320 from the received module data packets 166 based on the respective data count values 318. At a predetermined waveform data interval, the patient monitor host 110 displays 420 the aligned waveform data on the display device 124.

The process 400 also includes extracting 422 any numeric parameter data 322 from each module data packet 166 received by the patient monitor host 110. As discussed above, the numeric parameter data generally does not need to be updated as often as the waveform data. Thus, each sensor modules 112, 114, 116, 118 sends the waveform data 320 at a waveform data interval (e.g., 50 milliseconds) and the numeric parameter data 322 at a parameter data interval (e.g., 1 second). The process 400 includes determining 424 whether the predetermined parameter data interval has lapsed. If the predetermined parameter data interval has not lapsed, the process 400 repeats. If, on the other hand, the predetermined parameter data interval has lapsed, the patient monitor host 110 updates 426 a display of the numeric parameter data on the display device 124. The process 400 then repeats.

Figure 5:
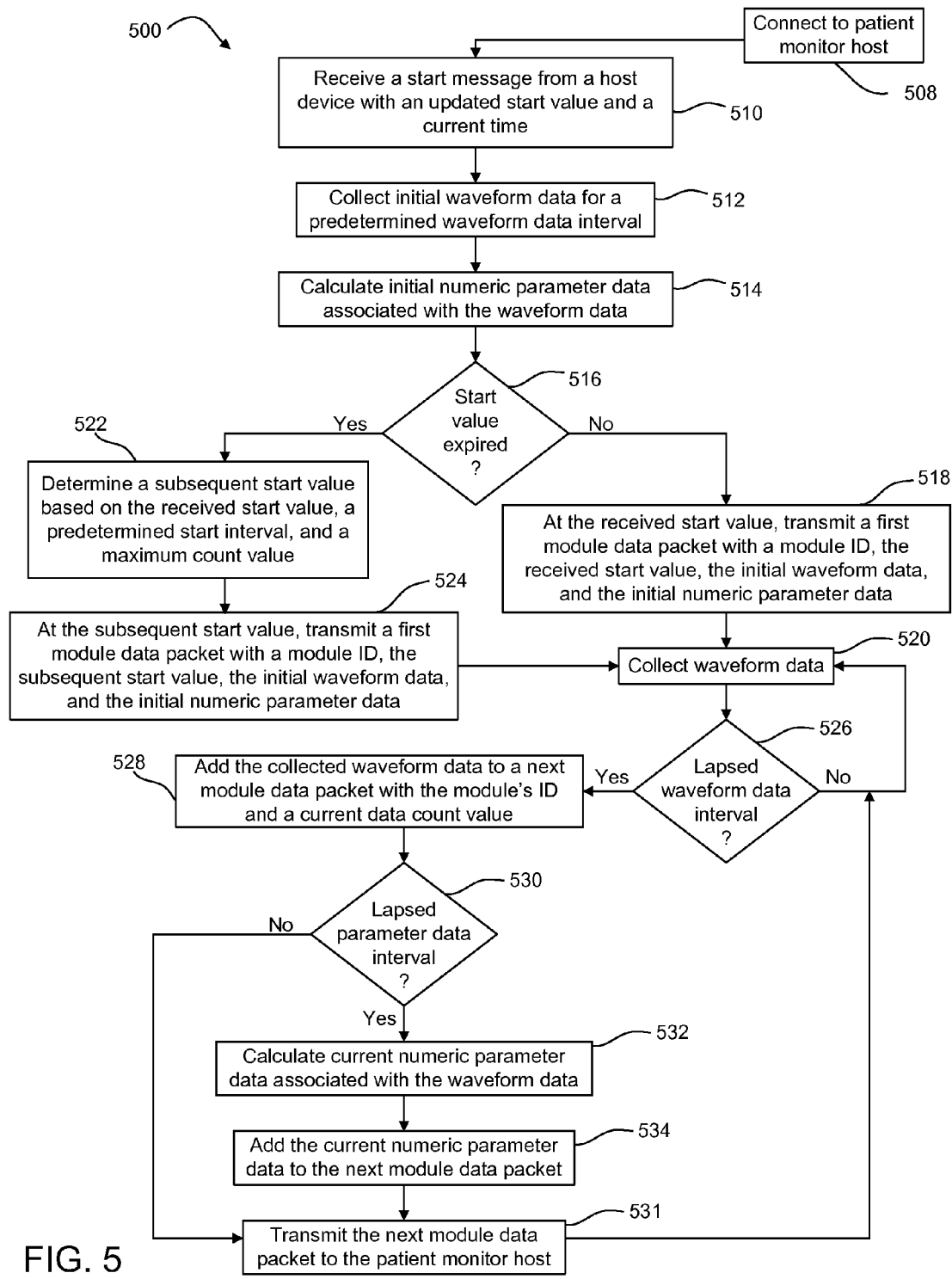
FIG. 5 is a flowchart of a process for synchronizing the communication of patient data in a patient monitor system according to one embodiment.

FIG. 5 is a flowchart of a process 500 for synchronizing the communication of patient data in a patient monitor system according to one embodiment. The process 500 may be performed, for example, by the sensor module 112 shown in FIG. 1. The process 500 includes connecting 508 to a patient monitor host, such as the patient monitor host 110 shown in FIG. 1. The process of connecting may include, for example, establishing a communication channel or otherwise using a communication protocol to establish communication between the sensor module 112 and the patient monitor host 110.

After establishing communications, the process 500 includes the sensor module 112 receiving 510 a start message 164 from the host device (such as the patient monitor host 110). As discussed above, the start message 164 includes an updated start value 310 and a current time 312. Although not shown in FIG. 5, the sensor module 112 continues to receive incrementing count values from the patient monitor host 110 at a predetermined count interval (e.g., 1 millisecond). The sensor module 112 then collects 512 initial waveform data for a predetermined waveform data interval (e.g., 50 milliseconds) and calculates 514 initial numeric parameter data associated with the collected waveform data.

The sensor module 112 then determines 516 whether the updated start value 310 received in the start message 164 has already expired. The updated start value 310 may pass by or expire, for example, due to excessive delays in receiving the start message 164 from the patient monitor host 110. Or, the updated start value 310 may expire while the sensor module 112 is collecting the initial waveform data. If the received updated start value 310 has not expired, then when the sensor module's counter is equal to the received updated start value 310, the sensor module 112 transmits 518 a first module data packet 166 with a module ID 316, the received updated start value 310, the initial waveform data, and the initial numeric parameter data. The process 500 continues by the sensor module 112 collecting 520 additional waveform data.

If, however, the received updated start value 310 expires before the initial waveform data can be collected and/or sent, the sensor module 112 determines 522 a subsequent start value based on the received updated start value 310, the predetermined start interval (e.g., 1 second), and a maximum count value (e.g., 2048 for an 11-bit counter). At the subsequent start value, the sensor module 112 transmits 524 a first module data packet 166 with a module ID 316, the subsequent start value, the initial waveform data, and the initial numeric parameter data. The process 500 continues by the sensor module 112 collecting 520 additional waveform data.

The sensor module 112 determines 526 whether the predetermined waveform data interval (e.g., 50 milliseconds) has lapsed. The sensor module 112 continues collecting 520 waveform data until the predetermined waveform data interval lapses. After the interval lapses, the sensor module 112 adds 528 the collected waveform data to a next module data packet 166 with the module's ID 316 and a current data count value 318. The current data count value 318 may be based on the sensor module's counter, which may be synchronized with the sequence count values received from the patient monitor host 110.

The sensor module 112 then determines 530 whether the predetermined parameter data interval (e.g., 1 second) has lapsed. If the predetermined parameter data interval has not lapsed, then the sensor module 112 transmits 531 the next module data packet 166 to the patient monitor host 110 and continues collecting 520 additional waveform data. If, however, the predetermined parameter data interval has lapsed, the sensor module 112 calculates 532 current numeric parameter data associated with collected waveform data and adds 534 the current numeric parameter data 322 to the next module data packet 166. The sensor module 112 then transmits 531 the next module data packet 166 to the patient monitor host 110 and continues collecting 520 additional waveform data.

Figure 6:
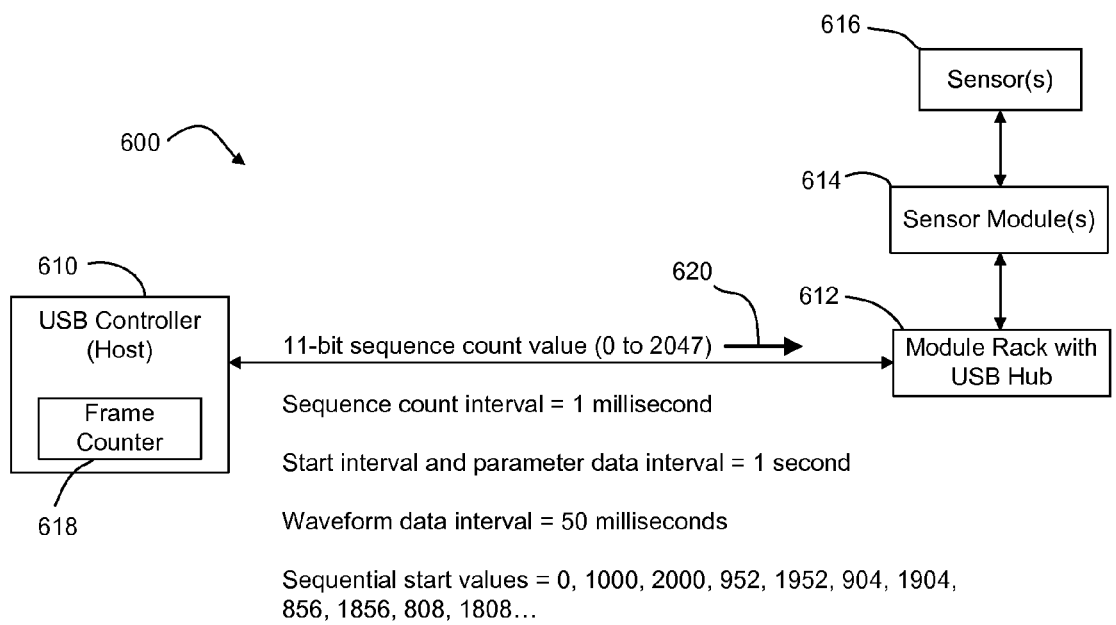
FIG. 6 is a block diagram of a patient monitor system with synchronized USB communication according to an example embodiment.

FIG. 6 is a block diagram of a patient monitor system 600 with synchronized USB communication according to an example embodiment. As discussed above, the disclosure herein is not limited to the numerical values and the use of USB devices described in this example embodiment. The system 600 includes a USB controller 610 that is located in a host. For example, the USB controller 610 may be located in the patient monitor host 110 shown in FIG. 1. The system 600 also includes a module rack 612 with a USB hub. The module rack 612 provides a docking region in this example embodiment for one or more sensor modules 614. As discussed above, each of the sensor modules 614 is connected to one or more sensors 616 that acquire patient data from a patient (not shown). An artisan will recognize from the disclosure herein that the USB controller 610 is not limited to communications with the single module rack 612. Rather, while not shown in FIG. 6 for illustrative purposes, the USB controller 610 may communicate with any number of module racks that function as USB hubs for respective sensor modules. In addition, or in other embodiments, the USB controller 610 may establish direct communications with USB enabled sensor modules without the need for a module rack.

The system 600 coordinates communications and events based on a USB frame count that is stored in a frame counter 618 of the USB controller 610. In this example embodiment, the frame counter 618 comprises an 11-bit hardware frame counter that counts from zero to 2047 and then rolls back over to zero again. An artisan will recognize from the disclosure herein that the frame counter 618 may be implemented with any number of bits to provide a maximum count value other than 2048. For example, in other embodiments, the frame counter 618 may be a 12-bit counter that counts from 0 to 4095, a 16-bit counter that counts from zero to 65,535, or a counter that uses any other number of bits. In other embodiments, the frame counter may 618 may be larger than an 11-bit counter, but only the lowest 11 bits are used to synchronize patient data. For example, in one embodiment, the frame counter 618 comprises a 32-bit hardware counter and the sensor modules 614 use the lowest 11 bits of the 32-bit count to determine when to transmit patient data to the USB controller 610.

In this example embodiment, the USB frame length is 1 millisecond. Thus, as shown by arrow 620 in FIG. 6, the USB controller 610 sends the incrementing frame count (i.e., the 11-bit sequence count value) to the module rack 612 at a sequence count interval of 1 millisecond. Different sequence count intervals may also be used. When using a high speed bus, for example, the USB controller 610 may send the 11-bit incrementing frame count every 125 microseconds. The 11-bit incrementing frame count may be sent by the USB controller 610 as part of, for example, a start of frame (SOF) token.

On registration of a newly connected sensor module 614, the USB controller 610 sends an updated start value corresponding to a value of the 11-bit incrementing frame count. The newly connected sensor module 614 begins sending data when the running 11-bit frame count is equal to the updated start value. The first data from the newly connected sensor module 614 includes waveform data and numeric parameter data. From then on, the newly connected sensor module 614, and every other connected sensor module 614, uses the millisecond count of the 11-bit incrementing frame count to send waveform data at a predetermined waveform data interval (e.g., 50 milliseconds) and the numeric parameter data at a predetermined parameter data interval (e.g., 1 second).

When a new USB enabled sensor module 614 establishes communications with the USB controller 610, the USB controller 610 instructs it to begin transmitting data (both waveform data and numeric parameter data) at the next 1-second boundary at which the other sensor modules 614 also transmit data (both waveform data and numeric parameter data). As discussed above, based on the 11-bit frame counter 618, the global 1-second boundary used for the sequential start values are: 0, 1000, 2000, 952, 1952, 904, 1904, 856, 1856, 808, 1808, . . . . By having the running 1-second start counter sent to each sensor module 614 on initialization, each sensor module 614 starts transmitting its respective waveform data and numeric parameter data on the same global 1-second boundary. Thereafter, each sensor module 614 sends data packets with waveform data every 50 milliseconds and data packets that include both waveform data and numeric parameter data at each global 1-second boundary.

Each sensor module 614 sends a copy of the 11-bit incrementing frame count with each of its data packets along with the collected data. The patient monitor host may indentify (and track) frame count values corresponding to 1-second boundaries in data packets returned from the sensor modules 614 by the fact that the sensor modules' data packets include numeric parameter data. By continually monitoring and updating the next 1-second boundary based on the 11-bit incrementing frame counts returned from the attached sensor modules 614, the proper 1-second boundary may be determined as an updated start value for any newly attached sensor modules 614. The patient monitor host uses the 11-bit incrementing frame counts returned from the attached sensor modules 614 to align waveform data from different sensor modules for display to a user, as disclosed herein.

It will be understood by those having skill in the art that many changes may be made to the details of the above-described embodiments without departing from the underlying principles of the invention. The scope of the present invention should, therefore, be determined only by the following claims.

The invention claimed is:

1. A patient monitor system for synchronizing a display of patient data, the system comprising:
a patient monitor host for receiving patient data sensed by a plurality of sensors attached to a patient, at least a first subset of the patient data arriving at the patient monitor host later than a second subset of the patient data, wherein the plurality of sensors sense the first and second subsets of the patient data within a global predetermined transmission period associated with an interval of sequence count values, the patient monitor host configured to:
transmit a first start value;
transmit sequence count values at a predetermined count interval, wherein the sequence count values are incremented at the predetermined count interval;
receive data packets including the patient data and data count values, the data count values corresponding to last received sequence count values at which the patient monitor host scheduled the respective data packets to be transmitted;
align the first subset of the patient data with the second subset of the patient data based on the respective data count values as end of measurement timings, the aligned first subset of the patient data and the aligned second subset of the patient data forming aligned patient data; and
display the aligned patient data on a display device; and
a plurality of sensor modules configured to selectively establish communications with the patient monitor host, the plurality of sensor modules respectively coupled to the plurality of sensors for acquiring the sensor data and for communicating the data packets to the patient monitor host, each of the plurality of sensor modules configured to start transmitting the data packets at the predetermined transmission period based on direct comparisons of the sequence count values to the first start value received from the patient monitor host.

2. The system of claim 1, wherein the patient monitor host comprises a sensor module interface configured to:
detect a new connection of a newly connected sensor module after transmission of the first start value;
in response to detecting the new connection, determine an updated start value based on a predetermined start interval and a maximum count value; and
transmit a start message to the newly connected sensor module with the updated start value,
wherein the newly connected sensor module is configured to start transmitting the data packets at the predetermined transmission period based on the direct comparisons of the sequence count values to the updated start value received from the patient monitor host.

3. The system of claim 2, wherein the sensor module interface comprises a counter for determining the sequence count values, wherein the maximum count value is based on a number of bits used by the counter, and wherein the counter rolls over to zero and continues counting after reaching the maximum count value.

4. The system of claim 2, wherein the patient data comprises waveform data and numeric parameter data, and wherein the predetermined start interval is equal to a predetermined parameter data interval at which the plurality of sensor modules transmit the numeric parameter data to the patient monitor host.

5. The system of claim 4, wherein the plurality of sensor modules are configured to transmit the waveform data to the patient monitor host at a predetermined waveform data interval that is less than the predetermined parameter data interval.

6. The system of claim 2, wherein the sensor module interface comprises a universal serial bus (USB) controller, and wherein the sequence count values comprise USB frame counts.

7. The system of claim 1, wherein the aligned patient data comprises waveform data.

8. The system of claim 7, wherein the patient monitor host updates the display of the aligned patient data based on a predetermined waveform data interval, and wherein the data count values corresponding to the transmitted sequence count values at which the patient monitor host expects the respective data packets to be transmitted are based on the predetermined waveform data interval.

9. The system of claim 7, wherein the patient monitor host is further configured to:
extract numeric parameter data from a subset of the received data packets; and
update, at a predetermined parameter data interval, a display of the numeric parameter data on the display device, wherein a subset of the data count values corresponding to the transmitted sequence count values at which the patient monitor host expects the respective data packets to be transmitted are based on the predetermined parameter data interval.

10. The system of claim 1, wherein each of the plurality of sensor modules is further configured to:
upon establishing communication with the patient monitor host, receive a start message from the patient monitor host with an updated start value;
collect initial waveform data from one or more of the sensors for a predetermined waveform data interval; and
calculate initial numeric parameter data associated with the initial waveform data.

11. The system of claim 10, wherein at least one of the plurality of sensor modules comprises a patient monitor interface configured to:
determine whether the received updated start value has expired based on the sequence count values transmitted by the patient monitor host; and
based on the determination of whether the received updated start value has expired, transmit an initial data packet including the initial waveform data and the initial numeric parameter data to the patient monitor host at a next start value.

12. The system of claim 11, wherein the initial data packet includes the next start value for use by the patient monitor host in aligning the initial waveform data with waveform data provided by the other sensor modules.

13. The system of claim 11, wherein the patient monitor interface is further configured to:
based on a current sequence count value received from the patient monitor host, determine that the received updated start value has expired; and
based on the determination that the received updated start value has expired, determine the next start value based on the received updated start value, a predetermined start interval, and a maximum count value.

14. The system of claim 11, wherein the patient monitor interface is further configured to:
based on a current sequence count value received from the patient monitor host, determine that the received updated start value has not expired; and based on the determination that the received updated start value has not expired, set the next start value equal to the received updated start value.

15. The system of claim 11, wherein the patient monitor interface is further configured to:
based on the waveform data interval, periodically transmit subsequent data packets to the patient monitor host comprising subsequently collected waveform data and a data count value corresponding to the transmitted sequence count values at which the patient monitor host expects the patient monitor interface to transmit a next set of waveform data.

16. The system of claim 11, wherein the patient monitor interface is further configured to:
determine that a predetermined parameter data interval has lapsed;
based on the determination that the predetermined parameter data interval has lapsed, add subsequent numeric parameter data to a subsequent data packet with subsequent waveform data; and
transmit the subsequent data packet to the patient monitor host.

17. The system of claim 11, wherein the patient monitor interface comprises a universal serial bus (USB) device, and wherein the sequence count values comprise USB frame counts, and wherein the first subset of the patient data and the second subset of patient data are aligned based on a USB frame count.

18. A method for synchronizing a display of patient data in a patient monitoring system, the method comprising:
acquiring, using a plurality of sensor modules, patient data sensed by a plurality of sensors, the plurality of sensor modules including a first sensor module and a second sensor module;
receiving the patient data from the plurality of sensor modules at a patient monitor host, at least a first subset of the patient data arriving at the patient monitor host later than a second subset of the patient data, wherein the first sensor module senses the first subset of the patient data within a global predetermined transmission interval defined by a starting sequence count value and an ending sequence count value, and wherein the second sensor module senses the second subset of the patient data within the same global predetermined transmission interval;
transmitting a first start value from the patient monitor host as a system start value;
transmitting sequence count values from the patient monitor host at a predetermined count interval, wherein the sequence count values are incremented at the predetermined count interval, the incrementing sequence count values forming a global time base with global synchronized time increments for the plurality of sensor modules;
receiving, at the patient monitor host, a first data packets from first sensor module, the first sensor module configured to start transmitting a first subset of data packets at the global predetermined transmission intervals based on direct comparisons of the sequence count values to the first start value received from the patient monitor host, the first data packet including the first subset of the patient data and a data count value, the data count value corresponding to a transmitted sequence count value at which the patient monitor host scheduled the first data packets to be transmitted;
receiving, at the patient monitor host, a second data packet from the second sensor module, the second sensor module configured to start transmitting a second subset of data packets at the global predetermined transmission intervals based on direct comparisons of the incrementing sequence count values to the first start value received from the patient monitor host, the second data packet including the second subset of patient data and the data count value corresponding to the transmitted sequence count value at which the patient monitor host scheduled the second data packet to be transmitted;
aligning the first subset of the patient data with the second subset of the patient data based on the data count value representing an end timing of measurement data; and
displaying the aligned patient data on a display device.

19. The method of claim 18, further comprising:
detecting, at the patient monitor host, a new connection of a newly connected sensor module after transmission of the first start value;
in response to detecting the new connection, determining an updated start value based on a predetermined start interval and a maximum count value; and
transmitting a start message to the newly connected sensor module with the updated start value,
wherein the newly connected sensor module is configured to start transmitting the data packets at the predetermined transmissions intervals based on direct comparisons of the sequence count values to the updated start value received from the patient monitor host.

20. The method of claim 19, wherein the patient data comprises waveform data and numeric parameter data, and wherein the predetermined start interval is equal to a predetermined parameter data interval at which the plurality of sensor modules transmit the numeric parameter data to the patient monitor host.

21. The method of claim 20, further comprising:
transmitting, from the plurality of sensor modules, the waveform data to the patient monitor host at a predetermined waveform data interval that is less than the predetermined parameter data interval.

22. The method of claim 18, wherein the aligned patient data comprises waveform data.

23. The method of claim 22, further comprising:
updating the display of the aligned patient data based on a predetermined waveform data interval, wherein the data count values corresponding to the transmitted sequence count values at which the patient monitor host scheduled the respective data packets to be transmitted are based on the predetermined waveform data interval.

24. The method of claim 22, further comprising:
extracting, at the patient monitor host, numeric parameter data from a subset of the received data packets; and
updating a display of the numeric parameter data on the display device, wherein a subset of the data count values corresponding to the transmitted sequence count values at which the patient monitor host expects the respective data packets to be transmitted are based on the predetermined parameter data interval.

25. The method of claim 18, further comprising:
upon establishing communication between a newly connected sensor module and the patient monitor host, receiving a start message at the newly connected sensor module from the patient monitor host with an updated start value;
collecting, at the newly connected sensor module, initial waveform data from one or more of the sensors for a predetermined waveform data interval;

calculating initial numeric parameter data associated with the initial waveform data;

determining whether the received updated start value has expired based on the sequence count values transmitted by the patient monitor host; and based on the determination of whether the received updated start value has expired, transmitting an initial data packet including the initial waveform data and the initial numeric parameter data from the newly connected sensor module to the patient monitor host at a next start value.

26. The method of claim 25, wherein the initial data packet includes the next start value for use by the patient monitor host in aligning the initial waveform data with waveform data provided by the other sensor modules.

27. The method of claim 25, further comprising:

based on a current sequence count value received at the newly connected sensor module from the patient monitor host, determining that the received updated start value has expired; and based on the determination that the received updated start value has expired, determining the next start value based on the received updated start value, a predetermined start interval, and a maximum count value.

28. The method of claim 25, further comprising:

based on a current sequence count value received at the newly connected sensor module from the patient monitor host, determining that the received updated start value has not expired; and based on the determination that the received updated start value has not expired, setting the next start value equal to the received updated start value.

29. The method of claim 25, further comprising:

based on the waveform data interval, periodically transmitting subsequent data packets from the newly connected sensor module to the patient monitor host comprising subsequently collected waveform data and a data count value corresponding to the transmitted sequence count values at which the patient monitor host expects the patient monitor interface to transmit a next set of waveform data.

30. The method of claim 25, further comprising:

determining that a predetermined parameter data interval has lapsed;

based on the determination that the predetermined parameter data interval has lapsed, adding subsequent numeric parameter data to a subsequent data packet with subsequent waveform data; and transmitting the subsequent data packet from the newly connected sensor module to the patient monitor host.

\* \* \* \* \*